United States Patent [19]
Stokes et al.

[11] Patent Number: 5,858,515
[45] Date of Patent: Jan. 12, 1999

[54] PATTERN-UNBONDED NONWOVEN WEB AND PROCESS FOR MAKING THE SAME

[75] Inventors: Ty Jackson Stokes, Suwanee; Cedric Arnett Dunkerly, II; Darryl Franklin Clark, both of Alpharetta, all of Ga.; Scot Patrick Honer, Corinth, Miss.

[73] Assignee: Kimberly-Clark Worldwide, Inc., Neenah, Wis.

Related U.S. Application Data

[60] Provisional application No. 60/009,459, Dec. 29, 1995.

[21] Appl. No.: 754,419

[22] Filed: Dec. 17, 1996

[51] Int. Cl.$^6$ .............................. B32B 27/14; D04H 3/08; A61F 13/15
[52] U.S. Cl. .......................... 428/195; 428/100; 428/219; 428/220; 442/361; 442/381; 442/394; 604/366; 604/391; 156/167; 156/181
[58] Field of Search .............................. 428/100, 99, 152, 428/198; 604/391, 366; 156/181, 167; 442/361, 381, 394

[56] References Cited

U.S. PATENT DOCUMENTS

| | | | |
|---|---|---|---|
| 4,082,886 | 4/1978 | Batterworth et al. | 428/284 |
| 4,115,620 | 9/1978 | Gupta et al. | 428/374 |
| 4,162,344 | 7/1979 | Rones | 428/212 |
| 4,172,172 | 10/1979 | Suzuki et al. | 428/224 |
| 4,211,819 | 7/1980 | Kunimune et al. | 428/374 |
| 4,290,174 | 9/1981 | Kalleberg | 24/204 |
| 4,306,929 | 12/1981 | Menikheim et al. | 156/290 |
| 4,355,066 | 10/1982 | Newman | 428/198 |
| 4,391,869 | 7/1983 | Cook et al. | 428/218 |
| 4,573,991 | 3/1986 | Pieniak et al. | 604/385 |
| 4,596,568 | 6/1986 | Flug | 604/369 |
| 4,600,618 | 7/1986 | Raychok, Jr. et al. | 428/92 |
| 4,668,552 | 5/1987 | Scott | 428/92 |
| 4,695,500 | 9/1987 | Dyer et al. | 428/134 |
| 4,704,117 | 11/1987 | Mitchell | 604/391 |

(List continued on next page.)

FOREIGN PATENT DOCUMENTS

| | | | |
|---|---|---|---|
| 0 091 419 | 10/1983 | European Pat. Off. | B62D 25/18 |
| 0 105 729 | 4/1984 | European Pat. Off. | D04H 1/54 |
| 0 138 549 | 4/1985 | European Pat. Off. | D04H 1/56 |
| 0 151 348 | 8/1985 | European Pat. Off. | B29C 61/06 |
| 0 169 868 | 2/1986 | European Pat. Off. | A41B 13/02 |

(List continued on next page.)

OTHER PUBLICATIONS

Patent Abstracts of Japan/Pub. No. 07313213/Pub. Date May 12, 1995.

*Primary Examiner*—Christopher Raimund
*Attorney, Agent, or Firm*—Nicholas N. Leach; James B. Robinson

[57] ABSTRACT

The present invention is directed to a pattern-unbonded nonwoven fabric having continuous bonded areas defining a plurality of discrete unbonded areas, which is suitable for use as an improved loop fastening material for hook and loop fastening systems. The fibers or filaments within the discrete unbonded areas of the present invention are dimensionally stabilized by the continuous bonded areas that encircle or surround each unbonded area. The spaces between fibers or filaments within the unbonded areas remain sufficiently open or large to receive and engage hook elements of a complementary hook material. The hook material can be any of a wide variety of commercially available hook components which, as is known in the art, typically include a base material from which a plurality of hook elements project. The present invention further is directed to a process for making such a pattern-unbonded nonwoven fabric including the steps of providing a nonwoven fabric or web, providing oppositely positioned first and second calender rolls and defining a nip therebetween, with at least one of said rolls being heated and having a bonding pattern on its outermost surface comprising a continuous pattern of land areas defining a plurality of discrete openings, apertures or holes, and passing the nonwoven fabric or web within the nip formed by said rolls.

21 Claims, 4 Drawing Sheets

U.S. PATENT DOCUMENTS

| | | | |
|---|---|---|---|
| 4,707,893 | 11/1987 | Hashizume et al. | 24/446 |
| 4,737,404 | 4/1988 | Jackson | 428/284 |
| 4,739,635 | 4/1988 | Conley et al. | 66/190 |
| 4,795,668 | 1/1989 | Krueger et al. | 428/174 |
| 5,119,643 | 6/1992 | Conley et al. | 66/190 |
| 5,614,281 | 3/1997 | Jackson et al. | 428/100 |

FOREIGN PATENT DOCUMENTS

| | | | |
|---|---|---|---|
| 0 173 058 | 3/1986 | European Pat. Off. | A61F 13/15 |
| 0 193 938 | 9/1986 | European Pat. Off. | B32B 27/10 |
| 0 211 564 | 2/1987 | European Pat. Off. | A44B 18/00 |
| 0 237 213 | 9/1987 | European Pat. Off. | B65D 65/40 |
| 0 240 213 | 10/1987 | European Pat. Off. | A61F 13/15 |
| 0 241 234 | 10/1987 | European Pat. Off. | C08J 5/18 |
| 0 252 743 | 1/1988 | European Pat. Off. | D04H 13/00 |
| 0 255 202 | 2/1988 | European Pat. Off. | D03D 27/00 |
| 0 278 866 | 8/1988 | European Pat. Off. | A44B 18/00 |
| 0 286 409 | 10/1988 | European Pat. Off. | B32B 27/12 |
| 0 289 198 | 11/1988 | European Pat. Off. | A44B 18/00 |
| 0 294 178 | 12/1988 | European Pat. Off. | B32B 27/12 |
| 0 321 234 | 6/1989 | European Pat. Off. | A61F 13/15 |
| 0 330 415 | 8/1989 | European Pat. Off. | D03D 15/00 |
| 0 360 208 | 3/1990 | European Pat. Off. | B32B 27/08 |
| 0 370 094 | 5/1990 | European Pat. Off. | A47G 9/00 |
| 0 389 611 | 10/1990 | European Pat. Off. | C08L 23/08 |
| 0 393 953 | 10/1990 | European Pat. Off. | A61F 13/60 |
| 0 415 758 | 3/1991 | European Pat. Off. | B32B 27/12 |
| 0 424 855 | 5/1991 | European Pat. Off. | B65D 81/26 |
| 0 431 504 | 6/1991 | European Pat. Off. | B32B 7/02 |
| 0 443 541 | 8/1991 | European Pat. Off. | B32B 7/00 |
| 0 474 376 | 3/1992 | European Pat. Off. | C08L 23/10 |
| 0 496 894 | 8/1992 | European Pat. Off. | B60R 21/16 |
| 0 497 608 | 8/1992 | European Pat. Off. | B32B 27/06 |
| 0 528 563 | 2/1993 | European Pat. Off. | C09J 7/02 |
| 0 536 323 | 4/1993 | European Pat. Off. | A61F 13/15 |
| 0 539 504 | 5/1993 | European Pat. Off. | A44B 18/00 |
| 0 563 284 | 10/1993 | European Pat. Off. | A44B 18/00 |
| 0 552 810 | 12/1993 | European Pat. Off. | D01F 6/30 |
| 0 575 123 | 12/1993 | European Pat. Off. | C08L 23/08 |
| 0 581 524 | 2/1994 | European Pat. Off. | B32B 5/04 |
| 0 581 570 | 2/1994 | European Pat. Off. | A44B 18/00 |
| 0 608 369 | 8/1994 | European Pat. Off. | C08F 10/00 |
| 0 616 618 | 9/1994 | European Pat. Off. | C08F 210/02 |
| 0 629 151 | 12/1994 | European Pat. Off. | B29C 55/00 |
| 0 662 988 | 7/1995 | European Pat. Off. | C08L 23/04 |
| 0 691 366 | 1/1996 | European Pat. Off. | C08J 5/18 |
| 0 677 553 | 5/1996 | European Pat. Off. | C08L 23/10 |
| 1 552 520 | 9/1979 | United Kingdom | D01F 8/06 |
| 2 048 168 | 12/1980 | United Kingdom | B32B 5/02 |
| 1 594 444 | 7/1981 | United Kingdom | D04H 3/14 |
| 2 105 758 | 3/1983 | United Kingdom | D04H 1/54 |
| 2 114 449 | 8/1983 | United Kingdom | A41B 13/02 |
| 2 160 586 | 12/1985 | United Kingdom | A44B 17/00 |
| 2 279 106 | 12/1994 | United Kingdom | A44B 18/00 |
| 87/05953 | 10/1987 | WIPO | D06N 3/04 |
| 91/12132 | 8/1991 | WIPO | B32B 5/24 |
| 92/01401 | 2/1992 | WIPO | A44B 18/00 |
| 92/15444 | 9/1992 | WIPO | B29C 55/18 |
| 92/20250 | 11/1992 | WIPO | A44B 18/00 |
| 92/20251 | 11/1992 | WIPO | A44B 18/00 |
| 93/07210 | 4/1993 | WIPO | C08L 23/08 |
| 93/21242 | 10/1993 | WIPO | C08F 210/16 |
| 94/07930 | 4/1994 | WIPO | C08F 299/00 |
| 94/14855 | 7/1994 | WIPO | C08F 4/628 |
| 94/18263 | 8/1994 | WIPO | C08J 5/18 |
| 94/28064 | 12/1994 | WIPO | C08L 23/04 |
| 94/01250 | 1/1995 | WIPO | B29C 47/00 |
| 95/03765 | 2/1995 | WIPO | A61F 13/15 |
| 95/04654 | 2/1995 | WIPO | B32B 27/12 |
| 95/05418 | 2/1995 | WIPO | C08L 23/04 |
| 95/07677 | 3/1995 | WIPO | A61F 13/62 |
| 95/09261 | 4/1995 | WIPO | D04H 1/54 |
| 95/11264 | 4/1995 | WIPO | C08F 10/02 |
| 95/25496 | 9/1995 | WIPO | A61F 13/62 |
| 95/30708 | 11/1995 | WIPO | C08J 5/18 |
| 95/33390 | 12/1995 | WIPO | A44B 18/00 |
| 96/11804 | 4/1996 | WIPO | B32B 27/12 |
| 96/16119 | 5/1996 | WIPO | C08L 23/04 |
| 96/23838 | 8/1996 | WIPO | C08L 23/10 |

PATTERN-UNBONDED NONWOVEN WEB AND PROCESS FOR MAKING THE SAME

This application claims priority from U.S. Provisional application No. 60/009,459 filed Dec. 29, 1995.

FIELD OF INVENTION

The present invention generally relates to the field of nonwoven fabrics and webs, and processes for manufacturing the same. More specifically, this invention relates to nonwoven fabrics and webs comprising continuous bonded areas defining a plurality of discrete, dimensionally-stabilized unbonded areas. Such nonwoven fabrics or webs made in accordance with the present invention are suitable for use as a loop fastening material for mechanical fastening systems, commonly referred to as hook and loop fastener systems.

BACKGROUND OF THE INVENTION

Mechanical fastening systems, of the type otherwise referred to as hook and loop fastener systems, have become increasingly widely used in various consumer and industrial applications. A few examples of such applications include disposable personal care absorbent articles, clothing, sporting goods equipment, and a wide variety of other miscellaneous articles. Typically, such hook and loop fastening systems are employed in situations where a refastenable connection between two or more materials or articles is desired. These mechanical fastening systems have in many cases replaced other conventional devices used for making such refastenable connections, such as buttons, buckles, zippers, and the like.

Mechanical fastening systems typically employ two components—a male (hook) component and a female (loop) component. The hook component usually includes a plurality of semi-rigid, hook-shaped elements anchored or connected to a base material. The loop component generally includes a resilient backing material from which a plurality of upstanding loops project. The hook-shaped elements of the hook component are designed to engage the loops of the loop material, thereby forming mechanical bonds between the hook and loop elements of the two components. These mechanical bonds function to prevent separation of the respective components during normal use. Such mechanical fastening systems are designed to avoid separation of the hook and loop components by application of a shear force or stress, which is applied in a plane parallel to or defined by the connected surfaces of the hook and loop components, as well as certain peel forces or stresses. However, application of a peeling force in a direction generally perpendicular or normal to the plane defined by the connected surfaces of the hook and loop components can cause separation of the hook elements from the loop elements, for example, by breaking the loop elements and thereby releasing the engaged hook elements, or by bending the resilient hook elements until the hook elements disengage the loop elements.

Mechanical fastening systems can be advantageously employed in disposable personal care absorbent articles, such as disposable diapers, disposable garments, disposable incontinence products, and the like. Such disposable products generally are single-use items which are discarded after a relatively short period of use—usually a period of hours—and are not intended to be washed and reused. As a result, it is desirable to avoid expensive components in the design of such products. Thus, to the extent that the hook and loop components are employed in such products, the hook and loop components need to be relatively inexpensive in terms of both the materials used and the manufacturing processes for making these components. On the other hand, the hook and loop components must have sufficient structural integrity and resiliency to withstand the forces applied thereto during normal wear of the absorbent article, in order to avoid potentially embarrassing situations for the wearer that can result from premature separation or disengagement of the hook and loop components.

U.S. Pat. No. 4,761,318 to Ott et al. discloses a loop fastening material useful in a mechanical fastening system for disposable articles. The loop fastening material disclosed by this patent includes a fibrous layer having a plurality of loops on a first surface adapted to be releasably engaged by a mating hook fastener portion and a layer of thermoplastic resin adhered to a second surface of the fibrous structure opposite the first surface. The thermoplastic resin anchors the loops in the fibrous structure.

U.S. Pat. No. 5,032,122 to Noel et al. discloses a loop fastening material useful in a mechanical fastening system for a disposable article. The loop fastening material disclosed by this patent includes a backing of orientable material and a multiplicity of fibrous elements extending from the backing. The fibrous elements are formed by continuous filaments positioned on and intermittently secured to the backing when the orientable material of the backing is in its dimensionally unstable state. The fibrous elements are formed by the shirring of the filaments between spaced, fixed regions of securement to the backing when the orientable material is caused to be transformed to its dimensionally stable state such that it is caused to contract or gather along its path of response. Thus, the loop material of this patent requires a backing of orientable material, such as an elastic or elastomeric or heat shrinkable material, that is caused to be transformed from a dimensionally stable state to a dimensionally unstable state and returned it to its dimensionally stable state.

U.S. Pat. No. 5,326,612 to Goulait discloses another a loop fastening material useful in a mechanical fastening system for a disposable article. The loop fastening material disclosed by this patent includes a nonwoven web secured to a backing. The nonwoven web serves to admit and entangle the hooks of a complementary hook component. The nonwoven web has a specified basis weight range of between about 5 to about 42 g/m$^2$, an inter-fiber bond area of less than about 10 percent, and a total plan view bonded area of less than about 35 percent.

Notwithstanding the teachings of the aforementioned references, the need nonetheless exists for an improved loop fastening material for a mechanical fastening system, particularly as such are used in disposable personal care absorbent articles. The pattern-unbonded nonwoven loop fastening material of the present invention is soft and cloth-like and, therefore, aesthetically appealing in terms of appearance and feel. The pattern-unbonded nonwoven fabric of the present invention has sufficient structural integrity and dimensional stability that, unlike certain of the prior art loop materials, the need for attachment to a support or backing layer to anchor the fibers or filaments within the nonwoven fabric is eliminated. The pattern-unbonded nonwoven fabric of the present invention is relatively inexpensive to produce, especially in comparison to conventional loop materials formed by knitting, warp knitting, weaving, and the like, yet exhibits satisfactory, comparable and/or improved peel and shear strengths as compared to conventional loop fastening materials when used with commercially available hook fastener materials.

SUMMARY OF THE INVENTION

The present invention is directed to a nonwoven fabric having continuous bonded areas defining a plurality of discrete unbonded areas, which is suitable for use as an improved loop fastening material for hook and loop fastening systems. The fibers or filaments within the discrete unbonded areas of the present invention are dimensionally stabilized by the continuous bonded areas that encircle or surround each unbonded area, such that no support or backing layer of film or adhesive is required. The unbonded areas are specifically designed to afford spaces between fibers or filaments within the unbonded areas that remain sufficiently open or large to receive and engage hook elements of a complementary hook material. The hook material can be any of a wide variety of commercially available hook components which, as is known in the art, typically include a base material from which a plurality of hook elements project.

The pattern-unbonded nonwoven fabric or web may be, for example, a spunbond nonwoven web formed of single component or multicomponent melt-spun filaments. At least one surface of the nonwoven fabric includes a plurality of discrete, unbonded areas surrounded or encircled by continuous bonded areas. The continuous bonded areas dimensionally stabilize the fibers or filaments forming the nonwoven web by bonding or fusing together the portions of the fibers or filaments that extend outside of the unbonded areas into the bonded areas, while leaving the fibers or filaments within the unbonded areas substantially free of bonding or fusing. The degree of bonding or fusing within the bonding areas desirably is sufficient to render the nonwoven web non-fibrous within the bonded areas, leaving the fibers or filaments within the unbonded areas to act as "loops" for receiving and engaging hook elements projecting from the hook material. As each discrete unbonded area is completely bounded by bonded areas, the fibers or filaments within the unbonded areas typically will have at least one portion thereof, and advantageously multiple portions thereof, extending into a bonded area. As a result, the unbonded fibers or filaments within each unbonded area acting as "loops" are less likely to be disengaged from or pulled out of the fibrous nonwoven web structure upon disengagement or removal of the hook elements of the hook material during normal use of the hook and loop fastening system. Thus, the pattern-unbonded nonwoven material of this invention, when used as a loop material, provides for a reduction in "fiber pull-out" by lessening the number of unattached, loose or unbonded fibers or filaments within the loop material. The pattern-unbonded nonwoven loop material exhibits improved surface integrity and durability, without otherwise deleteriously affecting the functionality of the nonwoven loop material with respect to peel and shear strengths.

Alternative embodiments of the above-described pattern-unbonded nonwoven fabric or web include laminates of two or more nonwoven webs or layers, laminates of two or more nonwoven webs or layers having different basis weights or wherein different fiber types and/or fiber sizes are used in forming the respective nonwoven webs or layers, and laminates of one or more nonwoven webs and a film layer.

A suitable process for forming the pattern-unbonded nonwoven material of this invention includes providing a nonwoven fabric or web, providing oppposedly positioned first and second calender rolls and defining a nip therebetween, with at least one of said rolls being heated and having a bonding pattern on its outermost surface comprising a continuous pattern of land areas defining a plurality of discrete openings, apertures or holes, and passing the nonwoven fabric or web within the nip formed by said rolls. Each of the openings in said roll or rolls defined by the continuous land areas forms a discrete unbonded area in at least one surface of the nonwoven fabric or web in which the fibers or filaments of the web are substantially or completely unbonded. Stated alternatively, the continuous pattern of land areas in said roll or rolls forms a continuous pattern of bonded areas that define a plurality of discrete unbonded areas on at least one surface of said nonwoven fabric or web. Alternative embodiments of the aforesaid process includes prebonding the nonwoven fabric or web before passing the fabric or web within the nip formed by the calender rolls, or providing multiple nonwoven webs to form a pattern-unbonded laminate.

When used as the loop component of a hook and loop fastening system for a disposable personal care absorbent article, the pattern-unbonded nonwoven loop material of this invention can be bonded or attached to the outer layer or backsheet of the article as a discrete patch of loop material. Alternatively, the pattern-unbonded nonwoven loop material can form the entire outer cover or backsheet of such a disposable personal care absorbent article.

DETAILED DESCRIPTION OF THE INVENTION

Figure 1:
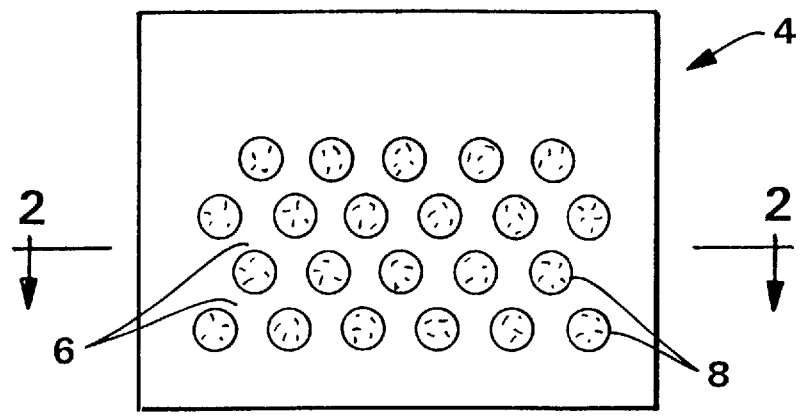
FIG. 1 is a top elevational view of the pattern-unbonded nonwoven fabric of the present invention.

The present invention relates to a nonwoven fabric or web having continuous bonded areas defining a plurality of discrete, unbonded areas, which is suitable for use as an improved loop fastening material for a mechanical or hook and loop fastening system. For purposes of illustration only, the present invention will be described as a loop fastening material both separately and in conjunction with its use with disposable personal care absorbent articles, which include diapers, training pants, incontinence garments, sanitary napkins, bandages and the like. As such, the invention should not be limited to these specific uses, as it is instead intended that the present invention be used in all applications in which such pattern-unbonded nonwoven fabric or web can be suitably employed.

For example, the pattern-unbonded nonwoven fabric or web of the present invention can be utilized as a filtration material, as well as a fluid management or distribution material for personal care absorbent articles, such as bodyside liners or surge materials used in disposable diapers and the like. The continuous bonded areas of the pattern-unbonded nonwoven web are substantially fluid impermeable, while the discrete unbonded areas of the web remain fluid permeable. Thus, the pattern-unbonded web includes discrete or isolated unbonded areas that function as specific fluid flow points or channels. The combination of continuous bonded areas and discrete unbonded areas within the pattern-unbonded web can be utilized to direct and channel fluid flow. Moreover, the pattern of continuous bonded areas and discrete unbonded areas can be modified to provide a variety of desired arrangements of flow points or channels for fluid filtration, management or distribution by modifying the pattern-unbonding assembly, as described in detail herein. Moreover, the three-dimensional surface topography of the pattern-unbonded fabric of the present invention can provide an aesthetically pleasing appearance for its user.

When used as the female or loop component of a hook and loop fastening system, the loop material of the present invention is intended to be utilized with a wide variety of hook materials. Exemplary of hook materials suitable for use with the loop material of the present invention are those obtained from: Velcro Group Company, of Manchester, N.H., H., under the trade designations CFM-22-1097; CFM-22-1121; CFM-22-1162; CFM-25-1003; CFM-29-1003; and CFM-29-1005; or Minnesota Mining & Manufacturing Co., of St. Paul, Minn., under the designation CS 200. Suitable hook materials generally comprise from about 16 to about 620 hooks per square centimeter, or from about 124 to about 388 hooks per square centimeter, or from about 155 to about 310 hooks per square centimeter. The hooks suitably have a height of from about 0.00254 centimeter (cm) to about 0.19 centimeter, or from about 0.0381 centimeter to about 0.0762 centimeter.

As is known in the art, hook materials typically include a base layer with a plurality of uni- or bi-directional hook elements extending generally perpendicularly therefrom. As used herein, the term "bi-directional" refers to a hook material having individual adjacent hook elements oriented in opposite directions in the machine direction of the hook material. The term "uni-directional," on the other hand, refers to a hook material having individual adjacent hook elements oriented in the same direction in the machine direction of the hook material.

In order to illustrate the pattern-unbonded nonwoven loop material of the present invention, the test data included hereinbelow was generated using a single type of hook material. This hook material includes hook elements having an average overall height measured from the top surface of the base material to the highest point on the hook elements. The average height of the hook elements used in conjunction with the present invention is about 0.5 millimeter (mm). This hook material has a hook density of about 265 hooks per square centimeter. The thickness of the base material is about 3.5 mils. This hook material is available from Velcro U.S.A. as CFM-29-1003. Other dimensions and properties of the hook material are as outlined in the examples described hereinbelow.

Although the term "hook material" is used herein to designate the portion of a mechanical fastening system having engaging (hook) elements, it is not intended to limit the form of the engaging elements to only include "hooks" but shall encompass any form or shape of engaging element, whether unidirectional or bi-directional, as is known in the art to be designed or adapted to engage a complementary loop fastening material, such as the pattern-unbonded nonwoven loop material of the present invention.

Figure 2:
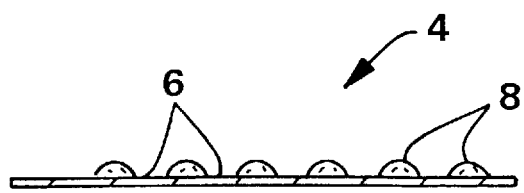
FIG. 2 is a cross-sectional side view of the pattern-unbonded nonwoven fabric of FIG. 1.

Referring to FIGS. 1 and 2, an embodiment of the pattern-unbonded nonwoven loop material 4 of the present invention is illustrated. By way of definition, the term "pattern-unbonded nonwoven loop material" as used herein is intended to refer to a loop or female component for a hook and loop fastening system that comprises, in its simplest form, a nonwoven fabric or web having continuous bonded areas 6 that define a plurality of discrete, dimensionally-stabilized unbonded areas 8. Within the continuous bonded areas 6, the fibers or filaments of the nonwoven web are thoroughly bonded or fused together, and desirably are non-fibrous, whereas within the unbonded areas 8 the fibers or filaments of the nonwoven fabric or web are substantially or completely free of bonding or fusing and retain their fibrous structure. This term is not intended to limit the loop material of the present invention to only nonwoven materials; rather, the loop material of the present invention can be advantageously employed in alternative embodiments in which, for example, the pattern-unbonded nonwoven fabric or web is attached or bonded to a layer of film material. Nor is use of the term "loop" intended to limit the loop material of the present invention to only materials in which discrete, separately formed loops of material are employed to receive and engage the hook elements of a complementary hook material; rather, the loop material of the present invention includes fibrous nonwoven fabrics or webs in which the individual fibers or filaments function to engage the hook elements without such fibers or filaments being formed into discrete loops.

As used herein, the terms "layer" or "web" when used in the singular can have the dual meaning of a single element or a plurality of elements. As used herein, the term "laminate" means a composite material made from two or more layers or webs of material which have been attached or bonded to one another.

Referring again to FIGS. 1 and 2, pattern-unbonded nonwoven loop material 4 can be generally described as any nonwoven fabric or web that, when formed in accordance with the present invention, is suitable for receiving and engaging the hooks of a complementary hook material. As used herein, the terms "nonwoven fabric" or "nonwoven web" mean a web having a structure of individual fibers or filaments that are interlaid, but not in an identifiable manner as in a knitted fabric. It should be noted, however, that although the present invention will be described in the context of nonwoven fabrics and webs, woven and/or knitted fabrics formed of appropriate materials such that a pattern of continuous bonded areas defining a plurality of discrete unbonded areas could be formed on at least one surface thereof can be dimensionally stabilized employing the process and apparatus described herein.

Commercially available thermoplastic polymeric materials can be advantageously employed in making the fibers or filaments from which pattern-unbonded nonwoven material 4 is formed. As used herein, the term "polymer" shall include, but is not limited to, homopolymers, copolymers, such as, for example, block, graft, random and alternating copolymers, terpolymers, etc., and blends and modifications thereof. Moreover, unless otherwise specifically limited, the term "polymer" shall include all possible geometrical configurations of the material, including, without limitation, isotactic, syndiotactic and random symmetries. As used herein, the terms "thermoplastic polymer" or "thermoplastic polymeric material" refer to a long-chain polymer that softens when exposed to heat and returns to its original state when cooled to ambient temperature. Exemplary thermoplastic materials include, without limitation, poly(vinyl chloride)s, polyesters, polyamides, polyfluorocarbons, polyolefins, polyurethanes, polystyrenes, poly(vinyl alcohol)s, caprolactams, and copolymers of the foregoing. The fibers or filaments used in making pattern-unbonded nonwoven material 4 may have any suitable morphology and may include hollow or solid, straight or crimped, single component, bicomponent or multicomponent, biconstituent or multiconstituent fibers or filaments, and blends or mixes of such fibers and/or filaments, as are well known in the art.

Nonwoven webs that can be employed as the pattern-unbonded nonwoven material of the present invention can be formed by a variety of known forming processes, including spunbonding, airlaying, or bonded carded web formation processes. All such nonwoven webs may be pre-bonded, using known nonwoven web bonding techniques, and subsequently bonded using the pattern-unbonded method and apparatus of the present invention, or alternatively, such nonwoven webs may only be bonded using the pattern-unbonded method and apparatus of this invention.

Spunbond nonwoven webs are made from melt-spun filaments. As used herein, the term "melt-spun filaments" refers to small diameter fibers and/or filaments which are formed by extruding a molten thermoplastic material as filaments from a plurality of fine, usually circular, capillaries of a spinnerette with the diameter of the extruded filaments then being rapidly reduced, for example, by non-eductive or eductive fluid-drawing or other well known spunbonding mechanisms. The production of spunbond nonwoven webs is described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,276,944 to Levy, U.S. Pat. No. 3,502,538 to Peterson, and U.S. Pat. No. 3,542,615 to Dobo et al., all of which are incorporated herein by reference. The melt-spun filaments formed by the spunbond process are generally continuous and have diameters larger than 7 microns, more particularly, between about 10 and 30 microns. Another frequently used expression of fiber or filament diameter is denier, which is defined as grams per 9000 meters of a fiber or filament. The spunbond filaments usually are deposited onto a moving foraminous belt or forming wire where they form a web. Spunbond filaments generally are not tacky when they are deposited onto the collecting surface.

Spunbond fabrics typically are stabilized or consolidated (pre-bonded) in some manner immediately as they are produced in order to give the web sufficient integrity to withstand the rigors of further processing into a finished product. This stabilization (prebonding) step may be accomplished through the use of an adhesive applied to the filaments as a liquid or powder which may be heat activated, or more commonly, by compaction rolls. As used herein, the term "compaction rolls" means a set of rollers above and below the web used to compact the web as a way of treating a just produced, melt-spun filament, particularly spunbond, web, in order to give the web sufficient integrity for further processing, but not the relatively strong bonding of secondary bonding processes, such as through-air bonding, thermal bonding, ultrasonic bonding and the like. Compaction rolls slightly squeeze the web in order to increase its self-adherence and thereby its integrity.

An alternative means for performing the pre-bonding step employs a hot air knife, as described in detail in the commonly assigned U.S. patent application Ser. No. 362, 328, filed Dec. 22, 1994, which is incorporated herein by reference. Briefly, the term "hot air knife" means a process of pre-bonding a just produced melt-spun filament, particularly spunbond, web, in order to impart the web with sufficient integrity, i.e., increase the stiffness of the web, for further processing, but not the relatively strong secondary bonding processes as noted above. A hot air knife is a device that focuses a stream of heated air at a very high flow rate, generally from about 300 to about 3000 meters per minute (mi/min.), or more particularly from about 900 to about 1500 m/min., directed at the nonwoven web immediately after its formation. The air temperature usually is in the range of the melting point of at least one of the polymers used in the web, generally between about 90° C. and about 290° C. for the thermoplastic polymers commonly used in spunbonding. The control of air temperature, velocity, pressure, volume and other factors helps avoid damage to the web while increasing its integrity. The hot air knife's focused stream of air is arranged and directed by at least one slot of about 3 to about 25 millimeters (mm) in width, particularly about 9.4 mm, serving as the exit for the heated air towards the web, with the slot running in a substantially cross-machine direction over substantially the entire width of the web. In other embodiments, there may be a plurality of slots arranged next to each other or separated by a slight gap. The at least one slot usually, but not necessarily, is continuous, and may be comprised of, for example, closely spaced holes. The hot air knife has a plenum to distribute and contain the heated air prior to its exiting the slot. The plenum pressure of the hot air knife usually is between about 2 to about 22 mmHg, and the hot air knife is positioned between about 6.35 mm and about 254 mm, and more particularly from about 19.05 to about 76.20 mm above the forming surface. In a particular embodiment, the hot air knife plenum's cross-sectional area for cross-directional flow (i.e., the plenum cross-sectional area in the machine direction) is at least twice the total slot exit area. Since the foraminous wire onto which spunbond polymer is formed generally moves at a high rate of speed, the time of exposure of any particular part of the web to the air discharge from the hot air knife typically is less than a tenth of a second and generally about one hundredth of a second, in contrast with the through-air bonding process, which has a much longer dwell time. The hot air knife process has a great range of variability and control over many factors, including air temperature, velocity, pressure, and volume, slot or hole arrangement, density and size, and the distance separating the hot air knife plenum and the web.

Figure 3:
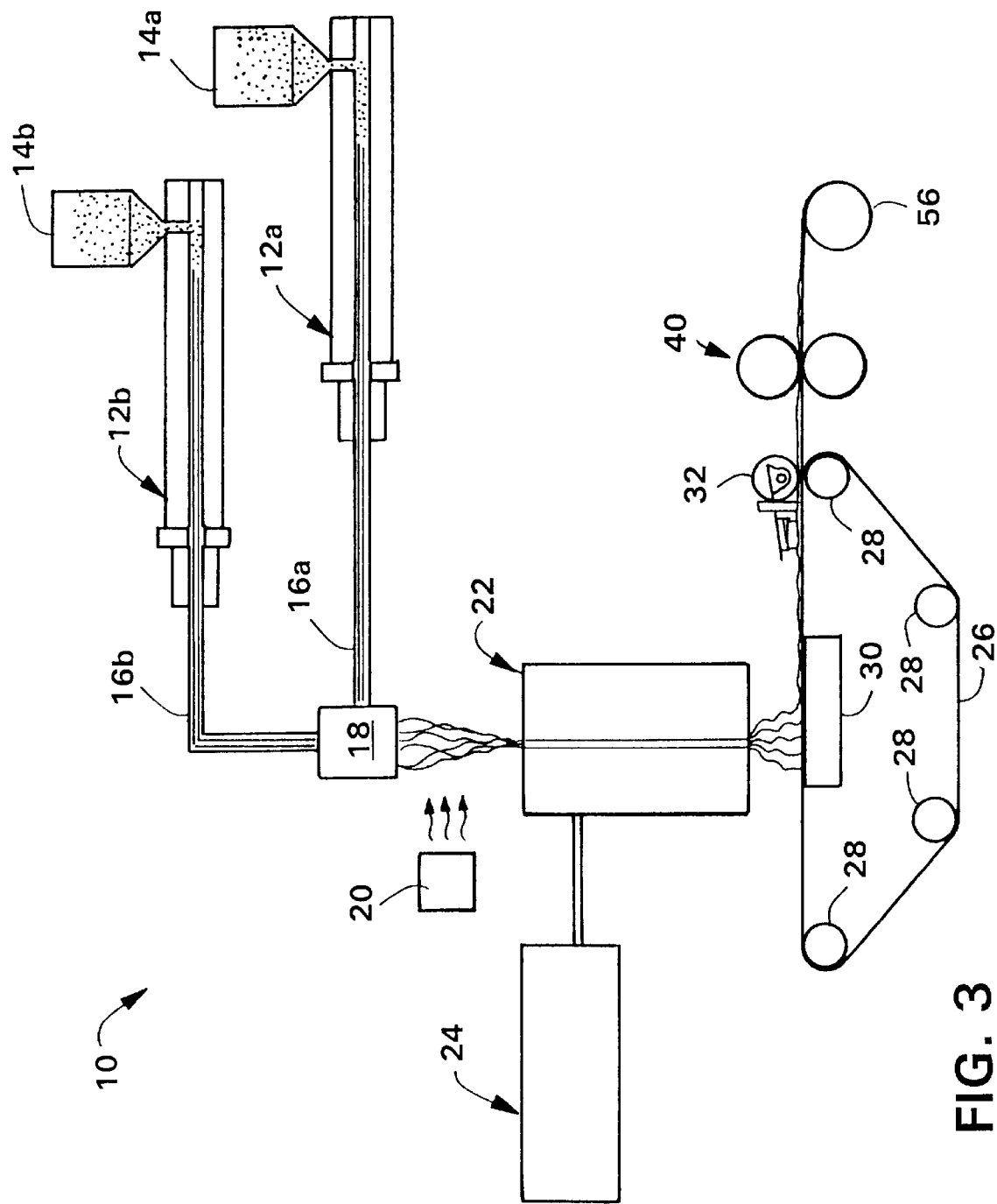
FIG. 3 is a schematic side view of an exemplary process and apparatus for producing a nonwoven web of spunbond bicomponent filaments.

The spunbond process also can be used to form bicomponent spunbond nonwoven webs as, for example, from side-by-side (or sheath/core) linear low density polyethylene/polypropylene spunbond bicomponent filaments. A suitable process for forming such bicomponent spunbond nonwoven webs is described in U.S. Pat. No. 5,418,045 to Pike et al., which is incorporated herein by reference in its entirety. Referring to FIG. 3 hereof, this process line 10 for forming such bicomponent filaments and resultant webs includes using a pair of extruders 12a and 12b for separately supplying both the polyethylene and the polypropylene from hoppers 14a and 14b, respectively, to a bicomponent spinnerette 18. Spinnerettes for producing bicomponent filaments are well known in the art and, therefore, are not described herein in detail. Generally, the spinnerette 18 includes a housing containing a spin pack, which includes a plurality of vertically stacked plates having a pattern of openings arranged to create flow paths for directing the high melting temperature and low melting temperature polymers separately to the fiber-forming openings in the spinnerette. The spinnerette 18 has openings arranged in one or more rows and the openings form a downwardly extending curtain of filaments when the polymers are extruded through the spinnerette. As the curtain of filaments exit the spinnerette 18, they are contacted by a quenching gas from one or both (not shown) sides of the filament curtain, which at least partially quenches the filaments and develops a latent helical crimp in the filaments extending from the spinnerette 18. Typically, the quenching air will be directed generally perpendicularly to the length of the filaments at a velocity of from about 30 to about 120 meters per minute and at a temperature of about 7° C. to about 32° C.

A fiber draw unit or aspirator 22 is positioned below the spinnerette 18 to receive the quenched filaments. Fiber draw units or aspirators for use in melt spinning polymers are well known in the art, as noted above. Exemplary fiber draw units suitable for use in this process include a linear fiber aspirator of the type shown in U.S. Pat. No. 3,802,817 to Matsuki et al., and eductive guns of the type shown in U.S. Pat. No. 3,692,618 to Dorschner et al. and U.S. Pat. No. 3,423,266 to Davies et al., the disclosures of which are incorporated herein by reference in their entirety. The fiber draw unit 22 in general has an elongated passage through which the filaments are drawn by aspirating gas flowing through the passage. The aspirating gas may be any gas, such as air, that does not adversely interact with the polymers of the filaments. A heater unit. As the aspiratiating gas to the fiber draw unit. As the aspirating gas draws the quenched filaments and ambient air through the fiber draw unit 22, the filaments are heated to a temperature that is required to activate the latent crimping therein. The temperature required to activate the latent crimping within the filaments will range from about 43° C. to a maximum of less than the melting point of the low melting component polymer which, in this case, is the polyethylene. Generally, a higher air temperature produces a higher number of crimps per unit length of the filament. Alternatively, the curtain of filaments exiting the spinnerette 18 may be drawn at ambient temperature, consequently forming a web of substantially straight or non-crimped spunbond filaments.

The drawn and crimped filaments exit the fiber draw unit 22 and are deposited onto a continuous forming surface 26 in a random manner, generally assisted by a vacuum device 30 placed underneath the forming surface. The purpose of the vacuum is to eliminate the undesirable scattering of the filaments and to guide the filaments onto the forming surface 26 to form a uniform unbonded nonwoven web of bicomponent filaments. If desired, the resultant web can be lightly compressed by a compression roller 32 or hot air knife (not shown) before the web is subjected to the pattern-unbonding assembly 34 of the present invention as described hereinbelow.

Suitable nonwoven webs for use in making the present invention also may be made from bonded carded webs and airlaid webs, which typically are formed of non-continuous, staple fibers. Care must be exercised when employing such nonwoven webs in making the pattern unbonded nonwoven loop material of the present invention to suitably adapt the size and density of the discrete, unbonded areas to maximize the number of individual fibers within the unbonded areas having at least one portion thereof, and advantageously multiple portions thereof, extending into the bonded areas.

Bonded carded webs are made from staple fibers, which are usually purchased in bales. The bales are placed in a picker, which separates the fibers. Then, the fibers are sent through a combing or carding unit, which further breaks apart and aligns the staple fibers in the machine direction to form a generally machine direction-oriented fibrous nonwoven web. Once the web is formed, it may be pre-bonded as described above.

Airlaying is another well known process by which fibrous nonwoven webs can be formed. In the airlaying process, bundles of small fibers having typical lengths ranging from about 6 to about 19 millimeters (mm) are separated and entrained in an air supply and then deposited onto a forming screen, usually with the assistance of a vacuum supply. The randomly deposited fibers then can be pre-bonded to one another using known bonding techniques.

Figure 4:
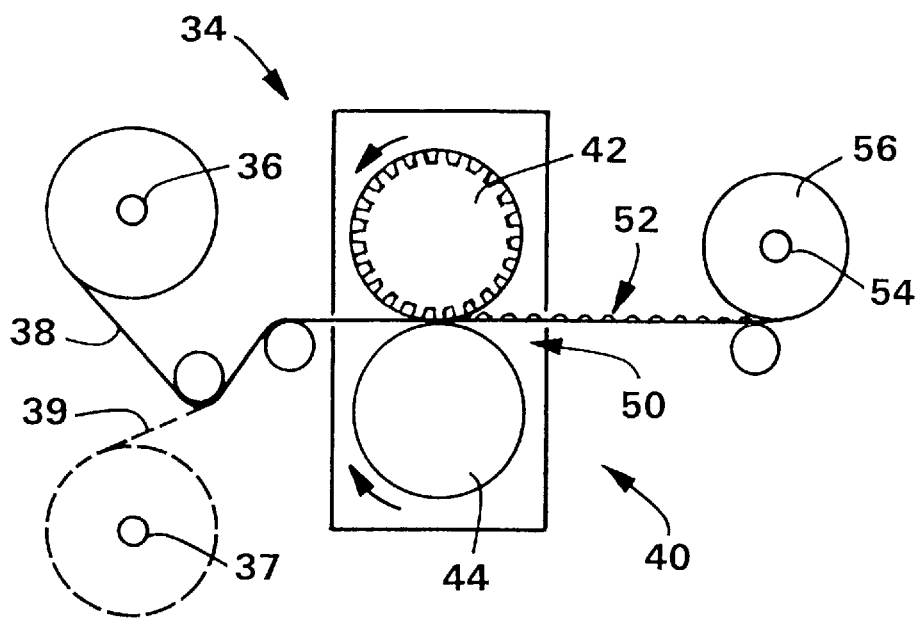
FIG. 4 is a schematic side view of a process and apparatus for making the pattern-unbonded nonwoven fabric of the present invention.
Figure 5:
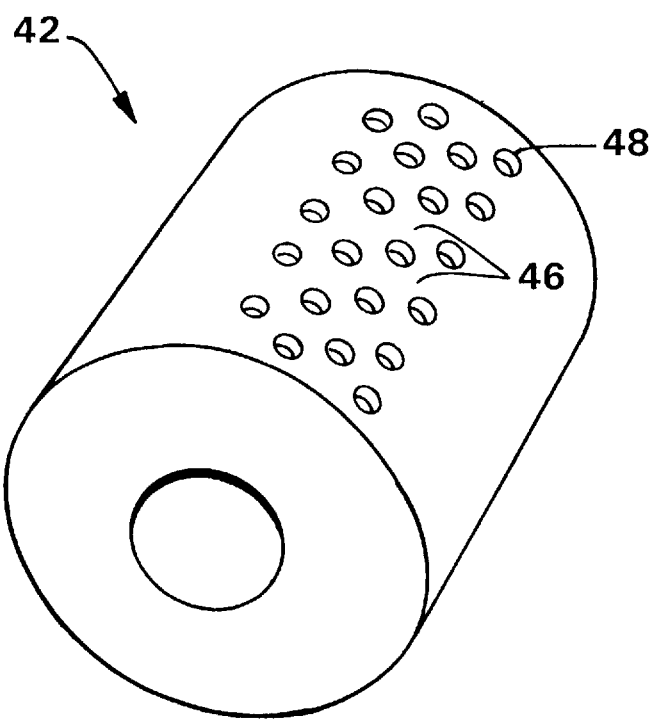
FIG. 5 is a partial perspective view of a pattern roll that can be used in accordance with the process and apparatus of FIG. 4.

After the nonwoven web is formed, the pre-bonded or unbonded web is passed through a suitable process and apparatus to form the pattern-unbonded nonwoven loop material of the present invention. Referring now to FIGS. 4 and 5, a process and apparatus for forming the pattern-unbonded nonwoven loop material of this invention now will be described. In FIG. 4, apparatus for forming the pattern-unbonded nonwoven loop material of this invention is represented generally as element 34. The apparatus includes a first web unwind 36 for a first web 38. Optionally, one or more additional web unwinds 37 (shown in phantom) for additional webs or layers 39 may be employed in forming multi-layer pattern-unbonded laminates. It should be understood that although the apparatus shown in FIG. 4 illustrates a web unwind 36, the pattern-unbonding assembly 40 may be placed in a continuous (in-line) process with the nonwoven forming equipment described herein, as shown in FIG. 3. As used herein, the term "pattern-unbonding assembly" should not be construed as apparatus for disassembling, destroying or removing existing bonds, if any, in web 38; rather, pattern-unbonding assembly refers to apparatus that continuously bonds or fuses the fibers or filaments forming web 38 in specified areas of the web, and prevents bonding or fusing of the fibers or filaments of web 38 in other specified areas of the web, such areas being referred to herein as bonded areas and unbonded areas, respectively.

First web 38 (or simply "web" if only one unwind is used) is taken off the unwind 36 and passed into a pattern-unbonding assembly 40 that includes a first or pattern roll 42 and a second or an anvil roll 44, both of which are driven by conventional drive means, such as, for example, electric motors (not shown). Pattern roll 42 is a right circular cylinder that may be formed of any suitable, durable material, such as, for example, steel, to reduce wear on the rolls during use. Pattern roll 42 has on its outermost surface a pattern of land areas 46 that define a plurality of discrete openings or apertures 48. The land areas 46 are designed to form a nip with the smooth or flat outer surface of opposedly positioned anvil roll 44, which also is a right circular cylinder that can be formed of any suitable, durable material.

The size, shape, number and configuration of openings 48 in pattern roll 42 can be varied to meet the particular end-use needs of the pattern-unbonded nonwoven loop material being formed thereby. In order to reduce the incidence of fiber pull-out in the resulting loop material, the size of openings 48 in pattern roll 42 should be dimensioned to reduce the likelihood that the entire length of the filaments or fibers forming an unbonded area will lie within a single unbonded area. Stated differently, fiber length should be selected to reduce the likelihood that the entire length of a given fiber or filament will fall within a single unbonded area. On the other hand, the desirability of restricting the size of the openings 48 in pattern roll 42, and the unbonded areas 8 formed thereby in the pattern-unbonded nonwoven loop material 4, is counter-balanced by the need for the unbonded areas 8 to have sufficient size to provide the required engagement areas for the hook elements of a complementary hook material. Circular openings 48 as shown in FIG. 5 hereof having an average diameter ranging from about 0.050 inch (about 0.127 cm) to about 0.250 inch (about 0.635 cm), and more specifically, from about 0.130 inch (0.330 cm) to about 0.160 inch (0.406 cm), and a depth measured from the outermost surface of pattern roll 42 of at least about 0.020 inch (about 0.051 cm), and more particularly at least about 0.060 inch (0.152 cm), are considered suitable in forming the pattern-unbonded nonwoven material of the present invention. While openings 48 in pattern roll 42 as shown in FIG. 5 are circular, other shapes, such as ovals, squares, diamonds and the like can be advantageously employed.

The number or density of openings 48 in pattern roll 42 also can be selected to provide the requisite amount of engagement areas for hook elements, without unduly limiting the size of the continuous bonded areas and giving rise to increased incidence of fiber pull-out. Pattern rolls having an opening density in the range of from about 1.0 opening per square centimeter ($cm^2$) to about 25.0 openings/$cm^2$, and more particularly from about 5.0 to about 7.0 openings/$cm^2$, may be utilized to advantage in forming the pattern-unbonded loop material of the present invention.

Moreover, the spacing between individual openings 48 can be selected to enhance the hook engagement functionality of the resulting pattern-unbonded loop material, without overly reducing the portion of the pattern-unbonded loop material occupied by continuous bonded areas, which serve to lessen fiber pull-out. Suitable inter-opening spacings for the embodiment shown can range from about 0.13 inch (about 3.30 mm) to about 0.22 inch (about 5.59 mm), centerline-to-centerline, in the machine and cross-machine directions. As used herein, the term "machine direction" or MD means the length of a material or fabric in the direction in which it is produced (from left to right in FIG. 3). The term "cross-machine direction" or CD means the width of a material or fabric, i.e., a direction generally perpendicular to the MD.

The particular arrangement or configuration of openings 48 in pattern roll 42 is not considered critical, so long as in combination with the opening size, shape and density, the desired levels of surface integrity and durability and hook element engagement are achieved. For example, as shown in FIG. 5, the individual openings 48 are arranged in staggered rows (see also FIG. 1). Other different configurations are considered within the scope of the present invention.

The portion of the outermost surface of the pattern roll 42 occupied by continuous land areas 46 likewise can be modified to satisfy the contemplated end-use application of the pattern-unbonded material. The degree of bonding imparted to the pattern-unbonded nonwoven loop material by the continuous land areas 46 can be expressed as a percent bond area, which refers to the portion of the total plan area of at least one surface of pattern-unbonded nonwoven loop material 4 (see FIG. 1) that is occupied by bonded areas 6. Stated generally, the lower limit on the percent bond area suitable for forming the pattern-unbonded nonwoven loop material 4 of the present invention is the point at which fiber pull-out excessively reduces the surface integrity and durability of the pattern-unbonded material. The required percent bond area will be affected by a number of factors, including the type(s) of polymeric materials used in forming the fibers or filaments of the nonwoven web, whether the nonwoven web is a single- or multi-layer fibrous structure, whether the nonwoven web is unbonded or pre-bonded prior to passing into the pattern-unbonding assembly, and the like. Pattern-unbonded nonwoven loop materials having percent bond areas ranging from about 25% to about 50%, and more particularly from about 36% to about 50%, have been found suitable.

The temperature of the outer surface of pattern roll 42 can be varied by heating or cooling relative to anvil roll 44. Heating and/or cooling can affect the features of the web(s) being processed and the degree of bonding of single or multiple webs being passed through the nip formed between the counterrotating pattern roll 42 and anvil roll 44. In the embodiment shown in FIG. 4, for example, both pattern roll 42 and anvil roll 44 are heated, desirably to the same bonding temperature. The specific ranges of temperatures to be employed in forming the pattern-unbonded nonwoven loop material hereof is dependent upon a number of factors, including the types of polymeric materials employed in forming the pattern-unbonded material, the inlet or line speed(s) of the nonwoven web(s) passing through the nip formed between pattern roll 42 and anvil roll 44, and the nip pressure between pattern roll 42 and anvil roll 44.

Anvil roll 42 as shown in FIG. 4 has an outer surface that is much smoother than pattern roll 42, and preferably is smooth or flat. It is possible, however, for anvil roll 44 to have a slight pattern on its outer surface and still be considered smooth or flat for purposes of the present invention. For example, if anvil roll 44 is made from or has a softer surface, such as resin impregnated cotton or rubber, it will develop surface irregularities, yet it will still be considered smooth or flat for purposes of the present invention. Such surfaces are collectively referred to herein as "flat." Anvil roll 44 provides the base for pattern roll 42 and the web or webs of material to contact. Typically, anvil roll 44 will be made from steel, or materials such as hardened rubber, resin-treated cotton or polyurethane.

Alternatively, anvil roll 44 may be replaced with a pattern roll (not shown) having a pattern of continuous land areas defining a plurality of discrete, apertures or openings therein, as in the above-described pattern roll 42. In such case, the pattern-unbonding assembly would include a pair of counter-rotating pattern rolls which would impart a pattern of continuous bonded areas defining a plurality of discrete unbonded areas on both the upper and lower surfaces of the pattern-unbonded nonwoven loop material. Rotation of the oppositely positioned pattern rolls can be synchronized, such that the resulting unbonded areas on the surfaces of the pattern-unbonded material are vertically aligned or juxtaposed.

Referring again to FIG. 4, pattern roll 42 and anvil roll 44 are rotated in opposite directions to one another so as to draw the nonwoven web (or webs) through the nip area defined therebetween. Pattern roll 42 has a first rotational speed measured at its outer surface and anvil roll 44 has a second rotational speed measured at its outer surface. In the embodiment shown, the first and second rotational speeds are substantially identical. However, the rotational speeds of the pattern and anvil rolls can be modified to create a speed differential between the counter-rotating rolls.

The locations of the oppositely positioned pattern roll 42 and anvil roll 44 may be varied to create a nip area 50 between the rolls. The nip pressure within nip area 50 can be varied depending upon the properties of the web itself or webs themselves and the degree of bonding desired. Other factors that will allow variances in the nip pressure will include the temperatures of the pattern roll 42 and anvil roll 44, the size and spacing of openings 48 in pattern roll 42, as well as the types of polymeric materials used in forming the pattern-unbonded nonwoven material. With respect to the degree of bonding to be imparted to the pattern-unbonded nonwoven loop material within the continuous bonded areas, the pattern-unbonded material desirably is thoroughly bonded or melt-fused in the bonded areas, such that the polymeric material is rendered non-fibrous. This high degree of bonding is important in stabilizing the portions of the fibers or filaments within the unbonded areas extending into the continuous bonded areas and reducing fiber pull-out when hook elements are disengaged from the discrete unbonded areas.

Figure 6:
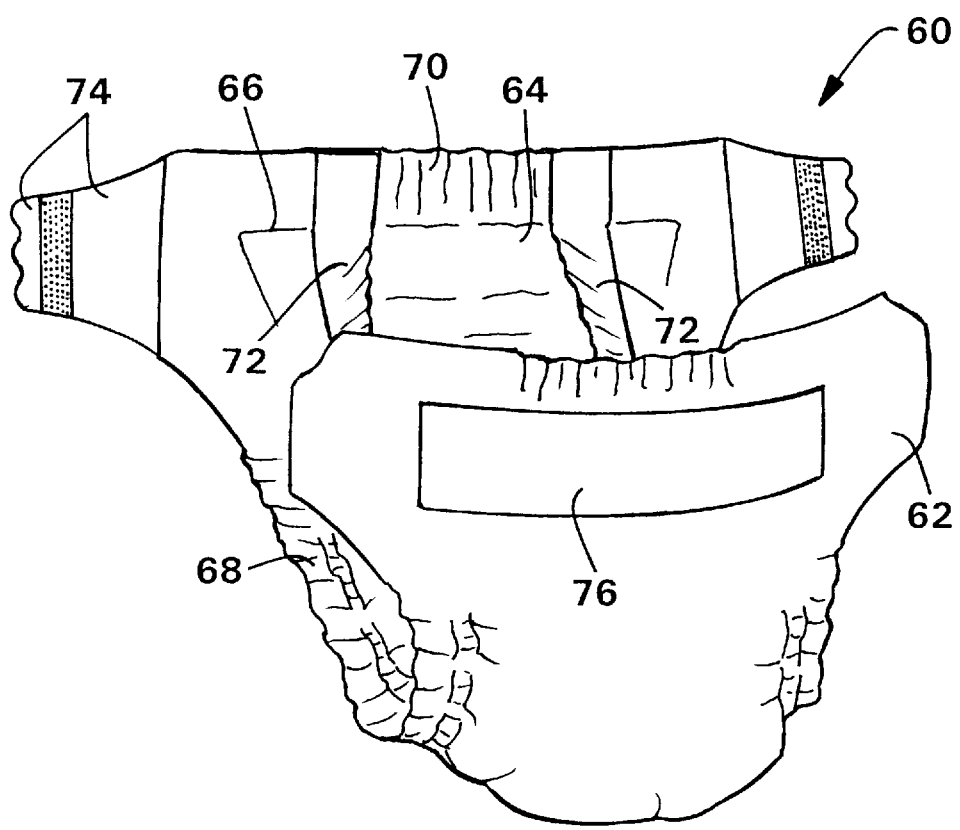
FIG. 6 is a perspective view of a disposable diaper with the pattern-unbonded nonwoven loop material of the present invention as a loop patch.

Once the pattern-unbonded nonwoven loop material of the present invention is formed, it can be attached to the outer cover or backsheet of a personal care absorbent article, such as disposable diaper 60 shown in FIG. 6. More specifically, pattern-unbonded loop material is attached to the outer surface such that the at least one surface of the pattern-unbonded loop material having a pattern of continuous bonded areas defining a plurality of discrete, unbonded areas is exposed. The pattern-unbonded loop material can be secured to outer cover 62 of diaper 60 by known attachment means, including adhesives, thermal bonding, ultrasonic bonding, or a combination of such means. A wide variety of adhesives can be employed, including, without limitation, solvent-based, water-based, hot-melt and pressure sensitive adhesives. Powdered adhesives can also be applied to the pattern-unbonded loop material and then heated to activate the powder adhesive and perfect bonding.

Diaper 60, as is typical for most personal care absorbent articles, includes a liquid permeable body side liner 64 and a liquid impermeable outer cover 62. Various woven or nonwoven fabrics can be used for body side liner 64. For example, the body side liner may be composed of a meltblown or spunbond nonwoven web of polyolefin fibers, or a bonded carded web of natural and/or synthetic fibers. Outer cover 62 is typically formed of a thin thermoplastic film, such as polyethylene film. The polymer film outer cover may be embossed and/or matte finished to provide a more aesthetically pleasing appearance. Other alternative constructions for outer cover 62 include woven or nonwoven fibrous webs that have been constructed or treated to impart the desired level of liquid impermeability, or laminates formed of a woven or nonwoven fabric and thermoplastic film. Outer cover 62 may optionally be composed of a vapor or gas permeable, "breathable" material, that is permeable to vapors or gas yet substantially impermeable to liquid. Breathability can be imparted in polymer films by, for example, using fillers in the film polymer formulation, extruding the filler/polymer formulation into a film and then stretching the film sufficiently to create voids around the filler particles, thereby making the film breathable. Generally, the more filler used and the higher the degree of stretching, the greater the degree of breathability.

Disposed between liner 64 and outer cover 62 is an absorbent core 66 formed, for example, of a blend of hydrophilic cellulosic woodpulp fluff fibers and highly absorbent gelling particles (e.g., superabsorbent). Absorbent core 66 is generally compressible, conformable, non-irritating to the wearers skin, and capable of absorbing and retaining liquid body exudates. For purposes of this invention, absorbent core 66 can comprise a single, integral piece of material, or a plurality of individual separate pieces of material. The size and absorbent capacity of absorbent core 66 should be compatible with the size of the intended user and the liquid loading imparted by the intended use of the diaper 60.

Elastic members may optionally be disposed adjacent each longitudinal edge 68 of diaper 60. Such elastic members are arranged to draw and hold the lateral, side margins 68 of diaper 60 against the legs of the wearer. Additionally, elastic members also may be disposed adjacent either or both of the end edges 70 of diaper 60 to provide an elasticized waistband.

Diaper 60 may further include optional containment flaps 72 made from or attached to body side liner 64. Suitable constructions and arrangements for such containment flaps are described, for example, in U.S. Pat. No. 4,704,116, to K. Enloe, the disclosure of which is incorporated herein by reference in its entirety.

To secure the diaper 60 about the wearer, the diaper will have some type of fastening means attached thereto. As shown in FIG. 6, the fastening means is a hook and loop fastening system including hook elements 74 attached to the inner and/or outer surface of outer cover 62 in the back waistband region of diaper 60 and one or more loop elements or patches 76 made from the pattern-unbonded loop material of the present invention attached to the outer surface of outer cover 62 in the front waistband region of diaper 60.

Having described the above embodiments of the present invention, a series of sample pattern-unbonded nonwoven loop materials, along with comparative prior art nonwoven materials, were formed to further illustrate the present invention. These samples were tested to determine peel strength and shear strength of the sample materials.

The peel strength of a loop material is a gauge of its functionality. More specifically, peel strength is a term used to describe the amount of force needed to pull apart the male and female components of a hook and loop fastening system. One way to measure the peel strength is to pull one component from the other at a 180 degree angle.

Shear strength is another measure of the strength of a hook and loop fastening system. Shear strength is measured by engaging the male and female components and exerting a force along the plane defined by the connected surfaces in an effort to separate the two components.

The test methods used to evaluate individual samples of the pattern-unbonded nonwoven loop material of the present invention are set forth below.

TEST METHODS

Basis Weight

The basis weights of various materials described herein were determined in accordance with Federal Test Method No. 191A/5041. Sample size for the sample materials was 15.24×15.24 centimeters and three values were obtained for each material and then averaged. The values reported below are for the average.

Bulk

The bulk of the sample materials, which is a measure of thickness, was measured at 0.5 psi with a Starret-type bulk tester.

180° Peel Strength Test

The 180° peel strength test involves attaching a hook material to a loop material of a hook and loop fastening system and then peeling the hook material from the loop material at a 180° angle. The maximum load needed to disengage the two materials is recorded in grams.

To perform the test, a continuous rate of extension tensile tester with a 5000 gram full scale load is required, such as a Sintech System 2 Computer Integrated Testing System available from Sintech, Inc., having offices in Research Triangle Park, N.C. A 75 mm by 102 mm sample of the loop material is placed on a flat, adhesive support surface. A 45 mm by 12.5 mm sample of hook material, which is adhesively and ultrasonically secured to a substantially inelastic, nonwoven material, is positioned over and applied to the upper surface of the loop material sample. To ensure adequate and uniform engagement of the hook material to the loop material, a 4½ pound hand roller is rolled over the combined hook and loop materials for one cycle, with one cycle equaling a forward and a backward stroke of the hand roller. One end of the fingertab material supporting the hook material is secured within the upper jaw of the tensile tester, while the end of the loop material directed toward the upper jaw is folded downward and secured within the lower jaw of the tensile tester. The placement of the respective materials within the jaws of the tensile tester should be adjusted such that minimal slack exists in the respective materials prior to activation of the tensile tester. The hook elements of the hook material are oriented in a direction generally perpendicular to the intended directions of movement of the tensile tester jaws. The tensile tester is activated at a crosshead speed of 500 mm per minute and the peak load in grams to disengage the hook material from the loop material at a 180° angle is then recorded.

Dynamic Shear Strength Test

The dynamic shear strength test involves engaging a hook material to a loop material of a hook and loop fastening system and then pulling the hook material across the loop material's surface. The maximum load required to disengage the hook from the loop is measured in grams.

To conduct this test, a continuous rate of extension tensile tester with a 5000 gram full scale load is required, such as a Sintech System 2 Computer Integrated Testing System. A 75 mm by 102 mm sample of the loop material is placed on a flat, adhesive support surface. A 45 mm by 12.5 mm sample of hook material, which is adhesively and ultrasonically secured to a substantially inelastic, nonwoven material, is positioned over and applied to the upper surface of the loop material sample. To ensure adequate and uniform engagement of the hook material to the loop material, a 4½ pound hand roller is rolled over the combined hook and loop materials for five cycles, with one cycle equaling a forward and a backward stroke of the hand roller. One end of the nonwoven material supporting the hook material is secured within the upper jaw of the tensile tester, and the end of the loop material directed toward the lower jaw is secured within the lower jaw of the tensile tester. The placement of the respective materials within the jaws of the tensile tester should be adjusted such that minimal slack exists in the respective materials prior to activation of the tensile tester. The hook elements of the hook material are oriented in a direction generally perpendicular to the intended directions of movement of the tensile tester jaws. The tensile tester is activated at a crosshead speed of 250 mm per minute and the peak load in grams to disengage the hook material from the loop material is then recorded.

EXAMPLES

A total of 18 sample pattern-unbonded nonwoven loop materials and 3 comparative nonwoven materials are set forth below. The sample pattern-unbonded materials are designed to illustrate particular embodiments of the present invention and to teach one of ordinary skill in the art the manner of carrying out the present invention. Comparative Examples A–C are designed to illustrate the advantages of the present invention.

The samples of the pattern-unbonded nonwoven loop materials all were formed using the process and apparatus described herein, and illustrated in FIGS. 3–5. In forming each sample pattern-unbonded material, the bicomponent spunbond web or laminate was passed through the nip formed between two counter-rotating thermal bonding rolls including a pattern roll and an anvil roll. The outer surface of the pattern roll included a pattern of land areas defining a plurality of discrete openings. The land areas occupied about 36% of the total area of the pattern roll outer surface. The openings in the pattern roll were circular, arranged in staggered rows, had an average diameter of 0.160 inch (0.406 cm), had a depth of 0.060 inch (0.152 cm), and had a density of about 5 openings/cm$^2$. Centerline-to-centerline spacings between openings were 0.165 inch (0.406 cm) in the machine direction and 0.190 inch (0.483 cm) in the cross-machine direction. The outer surface of the anvil roll was substantially smooth.

Comparative Examples A–C

Three single-layer bicomponent spunbond nonwoven webs of differing basis weights were formed of continuous melt-spun, crimped bicomponent filaments, as described in U.S. Pat. No. 5,418,045 to Pike et al. The polymeric components of the bicomponent filaments were present in a 50:50 ratio by weight, arranged in a side-by-side configuration. The bicomponent filaments had a substantially circular cross-section. The polymeric components were a) 98% Exxon Chemical Co. 3445 polypropylene and 2% titanium dioxide ($TiO_2$), and b) 98% Dow 6811A linear low density polyethylene (LLDPE) and 2% $TiO_2$, in which $TiO_2$ represents a concentrate comprising 50% by weight $TiO_2$ and 50% by weight polypropylene. The quench air temperature below the spinnerette was about 59° F. (15° C.), and the draw air temperature entering the fiber draw unit was about 350° F. (177° C.). The bicomponent spunbond webs were thermally point-bonded after formation to yield a point-bonded nonwoven material having a total bond area of about 15%.

Example A

The single-layer bicomponent spunbond nonwoven web of Comparative Example A was formed into a pattern-unbonded nonwoven loop material using the pattern-unbonding assembly described herein. Both the pattern roll and anvil roll were heated to a temperature of about 259° F. (about 126° C.). The nip pressure within the nip formed between the pattern roll and the anvil roll was about 40 pounds per square inch (psi) (about 28 kilogram per square centimeter (kg/cm$^2$)). After subjecting the materials of Comparative Example A and Example A to the above-described peel and shear tests, the latter material showed significantly fewer loose filaments within the unbonded areas, evidencing the reduction in fiber pull-out resulting from use of the present invention.

Example B

The single-layer bicomponent spunbond nonwoven web of Comparative Example B was formed into a pattern-unbonded nonwoven loop material using the pattern-unbonding assembly described herein. Pattern-unbonding processing conditions were as stated in Example A above, except both the pattern roll and anvil roll were heated to a temperature of about 263° F. (about 128° C.). After subjecting the materials of Comparative Example B and Example B to the above-described peel and shear tests, the latter material showed significantly fewer loose filaments within the unbonded areas, evidencing the reduction in fiber pull-out resulting from use of the present invention.

Example C

The single-layer bicomponent spunbond nonwoven web of Comparative Example C was formed into a pattern-unbonded nonwoven loop material using the pattern-unbonding assembly described herein. Pattern-unbonding processing conditions were as stated in Example A above. After subjecting the materials of Comparative Example C and Example C to the above-described peel and shear tests, the latter material showed significantly fewer loose filaments within the unbonded areas, evidencing the reduction in fiber pull-out resulting from use of the present invention.

Example D

A single-layer bicomponent spunbond nonwoven web was formed of continuous melt-spun, crimped bicomponent filaments, as described in U.S. Pat. No. 5,418,045. The polymeric components of the bicomponent filaments were the same as in the above Examples. The bicomponent spunbond web was not thermally point-bonded after formation.

The single-layer bicomponent spunbond web was formed into a pattern-unbonded nonwoven loop material using the pattern-unbonding assembly described herein. The pattern roll and anvil roll were heated to a temperature of about 270° F. (about 132° C.), the nip pressure within the nip formed between the pattern roll and the anvil roll was about 70 psi (about 49 kg/cm$^2$), and the line speed of the bicomponent spunbond web entering the nip was about 62 feet per minute (about 19 meters per minute).

Example E

A single-layer bicomponent spunbond nonwoven web was formed as stated above in Example D and formed into a pattern-unbonded nonwoven loop material using the pattern-unbonding assembly described herein. Pattern-unbonding processing conditions were as stated in Example D above, except the line speed of the bicomponent spunbond web entering the nip was about 148 feet per minute (about 45 meters per minute).

Example F

A two-layer nonwoven laminate material was made using first and second bicomponent spunbond nonwoven webs formed of continuous melt-spun, crimped bicomponent filaments, as described in U.S. Pat. No. 5,418,045. The polymeric components of the bicomponent filaments of the individual nonwoven layers were the same as in the above Examples. Neither bicomponent spunbond web was thermally point-bonded after formation. In this Example, the basis weights of, and the sizes of the bicomponent filaments forming, the first and second bicomponent spunbond webs were the same.

The first bicomponent spunbond nonwoven web was formed into a pattern-unbonded nonwoven layer using the pattern-unbonding assembly described herein. Then, the second bicomponent spunbond nonwoven web was formed and laid on top of the first pattern-unbonded nonwoven layer and the first and second nonwoven layers were laminated together by passing through the pattern-unbonding assembly described herein. Pattern-unbonding processing conditions were as stated in Example D above.

Example G

A two-layer nonwoven laminate material was made using a first bicomponent spunbond nonwoven web formed of continuous melt-spun, non-crimped bicomponent filaments, and a second bicomponent spunbond nonwoven web formed of continuous melt-spun, crimped bicomponent filaments, as described in U.S. Pat. No. 5,418,045. The polymeric components of the bicomponent filaments of the individual nonwoven webs were the same as in the above Examples. Neither bicomponent spunbond web was thermally point-bonded after formation. In this Example, the basis weights of, and the sizes of the bicomponent filaments forming, the first and second bicomponent spunbond webs differed.

The first, lower basis weight, lower fiber size, bicomponent spunbond nonwoven web was formed into a pattern-unbonded nonwoven layer using the pattern-unbonding assembly described herein. Then, the second, higher basis weight, higher fiber size, bicomponent spunbond nonwoven web was formed and laid on top of the first pattern-unbonded nonwoven layer. The second bicomponent spunbond layer was pre-bonded using a hot air knife positioned about 1.5 inches (about 38.1 mm) above the exposed surface of the second spunbond layer. The hot air knife directed a stream of air heated to a temperature of about 412° F. (about 211° C.) across the width of the spunbond webs. The plenum pressure of the hot air knife was about 2 mmHg. The first and second nonwoven layers were laminated together by passing through the pattern-unbonding assembly described herein. Pattern-unbonding processing conditions were as stated in Example D above, except the pattern roll and anvil roll were heated to a temperature of about 263° F. (about 128° C.). When tested for peel and shear strength, the second bicomponent spunbond nonwoven web was engaged with the hook elements of the test hook material.

Example H

A single-layer bicomponent spunbond nonwoven web was formed of continuous melt-spun, crimped bicomponent filaments, as described in U.S. Pat. No. 5,418,045. The polymeric components of the bicomponent filaments were the same as in the above Examples. The bicomponent spunbond web was pre-bonded with a hot air knife positioned about 1.75 inches (about 44.5 mm) above the upper surface of the bicomponent spunbond web. The hot air knife directed a stream of air heated to a temperature of about 412° F. (about 211° C.) across the width of the spunbond web. The plenum pressure of the hot air knife was about 2 mmHg. The bicomponent spunbond web was not thermally point-bonded after formation.

The single-layer bicomponent spunbond web was formed into a pattern-unbonded nonwoven loop material using the pattern-unbonding assembly described herein. Pattern-unbonding process conditions were as stated in Example G above, except the line speed of the bicomponent spunbond web entering the nip was about 47 feet per minute (about 14 meters per minute).

Example I

A two-layer nonwoven laminate material was made using a first bicomponent spunbond nonwoven webs formed of continuous melt-spun, non-crimped bicomponent filaments, and a second bicomponent spunbond nonwoven web formed of continuous melt-spun, crimped bicomponent filaments, as described in U.S. Pat. No. 5,418,045. The polymeric components of the bicomponent filaments of the individual nonwoven layers were the same as in the above Examples. Neither bicomponent spunbond web was thermally point-bonded after formation. In this Example, the basis weights of, and the sizes of the bicomponent filaments forming, the first and second bicomponent spunbond webs differed.

The first, lower basis weight, lower fiber size, bicomponent spunbond nonwoven web was formed. Then, the second, higher basis weight, higher fiber size, bicomponent spunbond nonwoven web was formed and laid on top of the first pattern-unbonded nonwoven layer. The second bicomponent spunbond web was pre-bonded as described above in Example G. Then, first and second nonwoven layers were laminated together by passing through the pattern-unbonding assembly described herein. Pattern-unbonding processing conditions were as stated in Example G above. When tested for peel and shear strength, the second bicomponent spunbond nonwoven web was engaged with the hook elements of the test hook material.

Example J

A two-layer nonwoven laminate material was made using a first bicomponent spunbond nonwoven webs formed of continuous melt-spun, non-crimped bicomponent filaments, and a second bicomponent spunbond nonwoven web formed of continuous melt-spun, crimped bicomponent filaments, as described in U.S. Pat. No. 5,418,045. The polymeric components of the bicomponent filaments of the individual nonwoven layers were the same as in the above Examples. Neither bicomponent spunbond web was thermally point-bonded after formation. In this Example, the basis weights of, and the sizes of the bicomponent filaments forming, the first and second bicomponent spunbond webs differed.

The first, lower basis weight, lower fiber size, bicomponent spunbond nonwoven web was formed. Then, the second, higher basis weight, higher fiber size, bicomponent spunbond nonwoven web was formed and laid on top of the first pattern-unbonded nonwoven layer. The second bicomponent spunbond web was pre-bonded as in Example G above, except the hot air knife was positioned about 1.06 inches (about 27.0 mm) above the exposed surface of the second nonwoven layer, and directed a stream of air heated to a temperature of about 245° F. (about 118° C.) across the widths of the nonwoven webs. The first and second nonwoven layers were laminated together by passing through the pattern-unbonding assembly described herein. Pattern-unbonding processing conditions were as stated in Example G above, except the pattern roll and anvil roll were heated to a temperature of about 280° F. (about 138° C.), and the nip pressure within the nip formed between the pattern roll and the anvil roll was about 80 psi (about 56 kg/cm$^2$). When tested for peel and shear strength, the second bicomponent spunbond nonwoven web was engaged with the hook elements of the test hook material.

Example K

A single-layer bicomponent spunbond nonwoven web was formed of continuous melt-spun, crimped bicomponent filaments, as described in U.S. Pat. No. 5,418,045. The polymeric components of the bicomponent filaments were the same as in the above Examples. The bicomponent spunbond web was pre-bonded with a hot air knife under the conditions set forth in Example J, except the hot air knife was positioned at a distance of about 1.5 inches (about 38.1 mm). The bicomponent spunbond web was not thermally point-bonded after formation.

The single-layer bicomponent spunbond web was formed into a pattern-unbonded nonwoven loop material using the pattern-unbonding assembly described herein. The pattern roll and anvil roll were heated to a temperature of about 260° F. (about 127° C.). Nip pressure within the nip formed between the pattern roll and the anvil roll was about 70 psi (about 49 kg/cm$^2$). The line speed of the bicomponent spunbond web entering the nip was about 42 feet per minute (about 13 meters per minute).

Example L

A two-layer nonwoven laminate material was made using a first bicomponent spunbond nonwoven webs formed of continuous melt-spun, non-crimped bicomponent filaments, and a second bicomponent spunbond nonwoven web formed of continuous melt-spun, crimped bicomponent filaments, as described in U.S. Pat. No. 5,418,045. The polymeric components of the bicomponent filaments of the individual nonwoven layers were the same as in the above Examples. Neither bicomponent spunbond web was thermally point-bonded after formation. In this Example, the basis weights of, and the sizes of the bicomponent filaments forming, the first and second bicomponent spunbond webs differed.

The first, lower basis weight, lower fiber size, bicomponent spunbond nonwoven web was formed. Then, the second, higher basis weight, higher fiber size, bicomponent spunbond nonwoven web was formed and laid on top of the first pattern-unbonded nonwoven layer. The second bicomponent spunbond web was pre-bonded using a hot air knife under the conditions stated for Example K above. The first and second nonwoven layers were laminated together by passing through the pattern-unbonding assembly described herein. The pattern roll and anvil roll were heated to a temperature of about 263 ° F. (about 128° C.). Nip pressure within the nip formed between the pattern roll and the anvil roll was about 80 psi (about 56 kg/cm$^2$). The line speed of the bicomponent spunbond web entering the nip was about 42 feet per minute (about 13 meters per minute). When tested for peel and shear strength, the second bicomponent spunbond nonwoven web was engaged with the hook elements of the test hook material.

Example M

A two-layer nonwoven laminate material was made using a first bicomponent spunbond nonwoven webs formed of continuous melt-spun, non-crimped bicomponent filaments, and a second bicomponent spunbond nonwoven web formed of continuous melt-spun, crimped bicomponent filaments, as described in U.S. Pat. No. 5,418,045. The polymeric components of the bicomponent filaments of the individual nonwoven layers were the same as in the above Examples. Neither bicomponent spunbond web was thermally point-bonded after formation. In this Example, the basis weights of, and the sizes of the bicomponent filaments forming, the first and second bicomponent spunbond webs differed.

The first, lower basis weight, lower fiber size, bicomponent spunbond nonwoven web was formed. Then, the second, higher basis weight, higher fiber size, bicomponent spunbond nonwoven web was formed and laid on top of the first pattern-unbonded nonwoven layer. The second bicomponent spunbond web was pre-bonded using a hot air knife under the same conditions as stated in Example L above. The first and second nonwoven layers were laminated together by passing through the pattern-unbonding assembly described herein. Pattern-unbonding processing conditions were as stated in Example L above, except the line speed of the bicomponent spunbond web entering the nip was about 68 feet per minute (about 21 meters per minute). When tested for peel and shear strength, the second bicomponent spunbond nonwoven web was engaged with the hook elements of the test hook material.

Example N

A single-layer bicomponent spunbond nonwoven web was formed of continuous melt-spun, crimped bicomponent filaments, as described in U.S. Pat. No. 5,418,045. The polymeric components of the bicomponent filaments were the same as in the above Examples. The bicomponent spunbond web was pre-bonded using a hot air knife under the conditions stated above for Example K, except the plenum pressure was about 2.6 mmHg. The bicomponent spunbond web was not thermally point-bonded after formation.

The single-layer bicomponent spunbond web was formed into a pattern-unbonded nonwoven loop material using the pattern-unbonding assembly described herein. The pattern roll and anvil roll were heated to a temperature of about 263° F. (about 128° C.). Nip pressure within the nip formed between the pattern roll and the anvil roll was about 80 psi (about 56 kg/cm$^2$). The line speed of the bicomponent spunbond web entering the nip was about 65 feet per minute (about 20 meters per minute).

Example O

A two-layer nonwoven laminate material was made using a first bicomponent spunbond nonwoven webs formed of continuous melt-spun, crimped bicomponent filaments, and a second bicomponent spunbond nonwoven web formed of continuous melt-spun, crimped bicomponent filaments, as described in U.S. Pat. No. 5,418,045. The polymeric components of the bicomponent filaments of the individual nonwoven layers were the same as in the above Examples. Neither bicomponent spunbond web was thermally point-bonded after formation. In this Example, the basis weights of, and the sizes of the bicomponent filaments forming, the first and second bicomponent spunbond webs differed.

The first, lower basis weight, lower fiber size, bicomponent spunbond nonwoven web was formed. Then, the second, higher basis weight, higher fiber size, bicomponent spunbond nonwoven web was formed and laid on top of the first pattern-unbonded nonwoven layer. The second bicomponent spunbond web was pre-bonded by passing the web through the nip formed between a pair of counter-rotating compaction or compression rolls. The nip pressure within the nip formed by the compaction rolls was about 75 psi (about 53 kg/cm$^2$). The first and second nonwoven layers were laminated together by passing through the pattern-unbonding assembly described herein. Pattern-unbonding processing conditions were as stated in Example M above. When tested for peel and shear strength, the second bicomponent spunbond nonwoven web was engaged with the hook elements of the test hook material.

Example P

A single-layer bicomponent spunbond nonwoven web was formed of continuous melt-spun, non-crimped bicomponent filaments, as described in U.S. Pat. No. 5,418,045. The polymeric components of the bicomponent filaments were the same as in the above Examples. The bicomponent spunbond web was pre-bonded with a hot air knife positioned at distance of about 1.125 inches (about 28.6 mm) from the upper surface of the web. The air stream exiting the hot air knife was at a temperature of about 245° F. (about 118° C.). The hot air knife had a plenum pressure of about 2 mmHg. The bicomponent spunbond web was not thermally point-bonded after formation.

The single-layer bicomponent spunbond web was formed into a pattern-unbonded nonwoven loop material using the pattern-unbonding assembly described herein. Pattern-unbonding processing conditions were substantially as stated in Example K above.

Example Q

A two-layer nonwoven laminate material was made using a first bicomponent spunbond nonwoven webs formed of continuous melt-spun, non-crimped bicomponent filaments, and a second bicomponent spunbond nonwoven web formed of continuous melt-spun, non-crimped bicomponent filaments, as described in U.S. Pat. No. 5,418,045. The polymeric components of the bicomponent filaments of the individual nonwoven layers were the same as in the above Examples. Neither bicomponent spunbond web was thermally point-bonded after formation. In this Example, the basis weights of, and the sizes of the bicomponent filaments forming, the first and second bicomponent spunbond webs differed.

The first, lower basis weight, lower fiber size, bicomponent spunbond nonwoven web was formed and pre-bonded using a hot air knife under the conditions stated in Example P above. Then, the second, higher basis weight, higher fiber size, bicomponent spunbond nonwoven web was formed and laid on top of the first pattern-unbonded nonwoven layer and the first and second nonwoven layers were laminated together by passing through the pattern-unbonding assembly described herein. Pattern-unbonding processing conditions were as stated in Example L above. When tested for peel and shear strength, the second bicomponent spunbond nonwoven web was engaged with the hook elements of the test hook material.

Example R

A single-layer bicomponent spunbond nonwoven web was formed of continuous melt-spun, crimped bicomponent filaments, as described in U.S. Pat. No. 5,418,045. The polymeric components of the bicomponent filaments were the same as in the above Examples. The bicomponent spunbond web was pre-bonded using a hot air knife as described above in Example P, except the distance from the surface of the web was about 0.5 inch (about 17.8 mm), and the plenum pressure was about 1.4 mmHg. The bicomponent spunbond web was not thermally point-bonded after formation.

The single-layer bicomponent spunbond web was formed into a pattern-unbonded nonwoven loop material using the pattern-unbonding assembly described herein. Pattern-unbonding processing conditions were substantially as stated in Example K above.

Example S

A two-layer nonwoven laminate material was made using bicomponent spunbond nonwoven webs of differing basis weights formed of continuous melt-spun, bicomponent filaments, as described in U.S. Pat. No. 5,418,045 to Pike et al. The polymeric components of the bicomponent filaments were present in a 50:50 ratio by weight, arranged in a side-by-side configuration. The bicomponent filaments had a substantially circular cross-section. The polymeric components were a) 99% Exxon Chemical Co. 3445 polypropylene and 1% titanium dioxide (TiO$_2$), and b) 78% Dow 6811A linear low density polyethylene (LLDPE) and 20% Shell Chemical Co.'s KRATON® G-2755 polymer and 2% optical brightener available from the Standridge Chemical Co. of Social Circle, Ga. as SCC-5348. KRATON® block copolymers are available in several different formulations, a number of which are identified in U.S. Pat. Nos. 4,663,220, 4,323,534, 4,834,738, 5,093,422 and 5,304,599, hereby incorporated by reference. The bicomponent spunbond webs were thermally point-bonded after formation to yield a point-bonded nonwoven material having a total bond area of about 35%.

The above-described sample and comparative materials had the following properties:

TABLE

| EXAMPLE | BASIS WEIGHT (gsm) | FIBER SIZE (dpf) | BULK (mils) | PERCENT BOND AREA (%) | SHEAR STRENGTH (grams) | PEEL STRENGTH (grams) | NUMBER OF REPETITIONS |
|---|---|---|---|---|---|---|---|
| COMP. A | 33.9 | 2.2 | 20 | 15 | 669 | 321 | 3 |
| A | 33.9 | 2.2 | 19 | 15/36 | 902 | 169 | 3 |
| COMP. B | 37.3 | 2.2 | 22 | 15 | 648 | 229 | 3 |
| B | 37.3 | 2.2 | 20 | 15/36 | 926 | 95 | 3 |
| COMP. C | 42.4 | 2.2 | 20 | 15 | 625 | 188 | 3 |
| C | 42.4 | 2.2 | 20 | 1536 | 954 | 101 | 3 |
| D | 50.9 | 3.3 | 25 | 36 | 1090 | 49 | 3 |
| E | 23.7 | 3.3 | 11 | 36 | 685 | 236 | 3 |
| F | 33.9/33.9 | 3.3/3.3 | 31 | 36/36 | 1710 | 293 | 3 |
| G | 50.9/17.0 | 7.6/2.3 | 43 | 36/36 | 1780 | 300 | 3 |
| H | 67.8 | 7.6 | 38 | 36 | 1912 | 256 | 3 |
| I | 50.9/17.0 | 10.4/2.3 | 44 | 36 | 1874 | 464 | 10 |
| J | 50.9/17.0 | 9.3/1.8 | 42 | 38 | 1680 | 370 | 3 |
| K | 50.9 | 9.2 | 35 | 36 | 1222 | 301 | 10 |
| L | 50.9/17.0 | 9.2/2.2 | 50 | 38 | 1599 | 418 | 10 |
| M | 42.4/17.0 | 9.2/2.2 | 38 | 36 | 1260 | 393 | 10 |
| N | 59.3 | 9.2 | 41 | 36 | 1212 | 267 | 10 |
| O | 50.9/17.0 | 9.2/2.2 | 50 | 36 | 2370 | 462 | 10 |
| P | 50.9 | 8.8 | 25 | 36 | 1168 | 222 | 10 |
| Q | 50.9/17.0 | 8.8/2.2 | 34 | 36 | 1607 | 253 | 10 |
| R | 50.9 | 8.8 | 40 | 36 | 1504 | 240 | 10 |
| S | 50.9/17.0 | 6–9/2–3 | NA | 38 | 5500 | 1300 | 6 |

Although specific values for peel and shear strength were provided for the above-described examples, the pattern-unbonded nonwoven loop material of the present invention should not be limited to such values. Generally, the pattern-unbonded loop material should have a combination of peel and shear strength that is suitable for its intended end use application. More specifically, peel strengths in the range of from about 50 grams to about 500 grams, or higher, are considered suitable for use in the present invention. Likewise, shear strengths ranging from about 600 grams to about 2500 grams, or higher, are considered suitable for use in the present invention. Likewise, the total basis weight of the pattern-unbonded loop material may be adapted to suit its intended end use application. Total basis weights in the range of from about 20 grams per square meter to about 100 grams per square meter, and more particularly in the range of from about 20 grams per square meter to about 70 grams per square meter, are considered suitable for use in the present invention.

It is contemplated that the pattern-unbonded nonwoven loop material constructed in accordance with the present invention will be tailored and adjusted by those of ordinary skill in the art to accommodate various levels of performance demand imparted during actual use. Accordingly, while this invention has been described by reference to the above embodiments and examples, it will be understood that this invention is capable of further modifications. This application is, therefore, intended to cover any variations, uses or adaptations of the invention following the general principles thereof, and including such departures from the present disclosure as come within known or customary practice in the art to which this invention pertains and fall within the limits of the appended claims.

We claim:

1. A pattern-unbonded nonwoven fabric comprising:
    a first nonwoven web having a fibrous structure of individual fibers or filaments;
    said nonwoven web having a bulk of at least about 10 mils and a basis weight of at least about 20 grams per square meter;
    said nonwoven web having on a surface thereof a pattern of continuous bonded areas defining a plurality of discrete unbonded areas formed by application of heat and pressure;
    said nonwoven web having a percent bond area of from about 25 percent to about 50 percent;
    said individual fibers or filaments within said discrete unbonded areas having at least a portion thereof extending into and bonded within said continuous bonded areas.

2. The pattern-unbonded nonwoven fabric of claim 1 where said nonwoven web has a percent bond area of from about 36 percent to about 50 percent.

3. The pattern-unbonded nonwoven fabric of claim 1 having a shear strength of at least about 600 grams and a peel strength of at least about 50 grams.

4. The pattern-unbonded nonwoven fabric of claim 1 wherein said nonwoven web comprises melt-spun filaments.

5. The pattern-unbonded nonwoven fabric of claim 1 wherein said nonwoven web comprises staple fibers.

6. The pattern-unbonded nonwoven fabric of claim 4 wherein said nonwoven web comprises melt-spun multi-component filaments.

7. The pattern-unbonded nonwoven fabric of claim 1 further comprising a film layer attached to a surface of said nonwoven opposite said surface having said pattern of continuous bonded areas defining said plurality of discrete unbonded areas.

8. The pattern-unbonded nonwoven fabric of claim 1 further comprising:
    a second nonwoven web having a fibrous structure of individual fibers or filaments;
    said first and second nonwoven webs being laminated together.

9. The pattern-unbonded nonwoven fabric of claim 8 wherein said individual fibers or filaments of said first nonwoven web have a first denier and said individual fibers or filaments of said second nonwoven web have a second denier different from said first denier, and wherein said first nonwoven web has a first basis weight and said second nonwoven web has a second basis weight different from said first basis weight.

10. A mechanical fastening system comprising:
    a male component; and
    a female component adapted for releasable engagement with said male component;

said female component comprising said pattern-unbonded nonwoven fabric of claim 1.

11. A disposable absorbent article comprising the pattern-unbonded nonwoven fabric of claim 1.

12. The disposable absorbent article comprising:

a bodyside liner;

an outer cover;

an absorbent structure disposed between said liner and said outer cover;

a mechanical fastening tab joined to said article, said fastening tab including a male component; and a female component joined to said outer cover and adapted for releasable engagement with said male component;

said female component comprising said pattern-unbonded nonwoven fabric of claim 1.

13. A process for forming a pattern-unbonded nonwoven fabric comprising the steps of:

forming a first nonwoven web having a fibrous structure of individual fibers or filaments;

feeding said nonwoven web into a nip defined between opposedly positioned first and second rolls, said first roll having a patterned outer surface and said second roll having a smooth outer surface;

rotating said first and second rolls in opposite directions;

bonding said nonwoven web by application of heat and pressure to form on a surface thereof a pattern of continuous bonded areas defining a plurality of discrete unbonded areas;

whereby said nonwoven web has a percent bond area of from about 25 percent to about 50 percent; and said individual fibers or filaments within said discrete unbonded areas have at least a portion thereof extending into and bonded within said continuous bonded areas.

14. The process of claim 13 further comprising the steps of feeding said nonwoven web into said nip defined between said first and second rolls, wherein said first and second rolls have patterned outer surfaces, and bonding said nonwoven web by application of heat and pressure to form on at least two surfaces thereof a pattern of continuous bonded areas defining a plurality of discrete unbonded areas.

15. The process of claim 13 further comprising the steps of:

forming a second nonwoven web having a fibrous structure of individual fibers or filaments;

feeding said first and second nonwoven webs into said nip; and bonding said first and second nonwoven web together to form a pattern-unbonded nonwoven laminate.

16. The process of claim 15 further comprising the steps of:

forming a first nonwoven web having a first fiber or filament size and a first basis weight;

forming a second nonwoven web having a second fiber or filament size different from said first fiber or filament size and a second basis weight different from said first basis weight.

17. The process of claim 13 further comprising the step of pre-bonding said first nonwoven web.

18. The process of claim 15 further comprising the step of pre-bonding at least one of said first and second nonwoven webs.

19. The process of claim 13 further comprising the step of forming said nonwoven layer comprising melt-spun filaments.

20. The process of claim 19 further comprising the step of forming said nonwoven layer comprising melt-spun multi-component filaments.

21. The process of claim 20 further comprising the step of forming said nonwoven layer comprising melt-spun multi-component crimped filaments.

* * * * *

UNITED STATES PATENT AND TRADEMARK OFFICE
CERTIFICATE OF CORRECTION

PATENT NO. : 5,858,515
DATED : January 12, 1999
INVENTOR(S) : Ty Jackson Stokes et al.

It is certified that error appears in the above-identified patent and that said Letters Patent is hereby corrected as shown below:

Column 9, Lines 24-25, "A heater unit. As the aspiratiating gas to the fiber draw unit." should read -- A heater 24 supplies hot aspirating gas to the fiber draw unit. --

Signed and Sealed this

Eleventh Day of May, 1999

Attest:

Q. TODD DICKINSON

*Attesting Officer*  *Acting Commissioner of Patents and Trademarks*